United States Patent [19]

Donohue

[11] Patent Number: 5,027,802

[45] Date of Patent: Jul. 2, 1991

[54] MULTI-MODE DIGITAL TRACTION SYSTEM

[76] Inventor: Patrick T. Donohue, 1822 NE. 143rd, Portland, Oreg. 97230

[21] Appl. No.: 367,251

[22] Filed: Jun. 16, 1989

[51] Int. Cl.[5] .................................................. A61F 5/04

[52] U.S. Cl. ...................................... 128/87 A; 128/77

[58] Field of Search .............. 128/75, 77, 87 A, 84 R, 128/87 R

[56] References Cited

U.S. PATENT DOCUMENTS

| | | | |
|---|---|---|---|
| 2,146,933 | 2/1939 | Budin | 128/81 |
| 2,237,251 | 4/1941 | Longfellow | 128/87 |
| 2,438,144 | 3/1948 | Bunyan | 128/77 |
| 2,646,794 | 7/1953 | Baer | 128/87 A |
| 3,547,112 | 12/1970 | Courtney | 128/77 |
| 3,850,166 | 11/1974 | Tamny et al. | 128/84 |
| 3,872,861 | 3/1975 | Tamny et al. | 128/84 |
| 4,602,620 | 7/1986 | Marx | 128/84 |
| 4,644,938 | 2/1987 | Yateo et al. | 128/77 |
| 4,724,827 | 2/1988 | Schenck | 128/26 |
| 4,765,320 | 8/1988 | Lindemann et al. | 128/87 A |
| 4,781,178 | 11/1988 | Gordon | 128/87 A X |
| 4,790,301 | 12/1988 | Silfverskiold | 128/87 A |
| 4,809,688 | 3/1989 | del Valle et al. | 128/88 |
| 4,945,902 | 8/1990 | Dorer et al. | 128/87 A |

FOREIGN PATENT DOCUMENTS

| | | | |
|---|---|---|---|
| 293622 | 8/1915 | Fed. Rep. of Germany | 128/87 A |
| 313177 | 8/1917 | Fed. Rep. of Germany | 128/77 |
| 0667397 | 10/1988 | Switzerland | 128/77 |
| 1323093 | 7/1987 | U.S.S.R. | 128/77 |
| 589416 | 6/1947 | United Kingdom | 128/87 A |
| 620852 | 4/1949 | United Kingdom | 128/87 A |

OTHER PUBLICATIONS

"1989 Orthopedics" catalog, p. B19, Fred Sammons, Inc., Burr Ridge, Ill., 1989.

*Primary Examiner*—Robert Bahr
*Attorney, Agent, or Firm*—Bruce J. Ffitch

[57] ABSTRACT

A digital traction system is disclosed in a hand application. A common traction plate spanning the length of the fingers and breadth of the hand may be mounted in a dorsal or is a palmar position. In the palmar position, the traction plate is anchored close to the base of the fingers or metacarpophalangeal joints by a hook and loop type fabric fastener such as that sold under the trademark VELCRO connecting the traction plate to a fingerless glove worn by the patient. Tension elements fastened to the traction plate are trained over rollers at the end of the plate and connected to finger traps which grip the patient's fingers. In the dorsal position the plate is anchored by lugs fixed to the plate and passing between the fingers and engaging the crotches between the fingers. An auxiliary traction plate allows the thumb to be treated independently of the fingers if desired.

26 Claims, 2 Drawing Sheets

MULTI-MODE DIGITAL TRACTION SYSTEM

BACKGROUND OF THE INVENTION

The invention concerns devices for applying therapeutic traction to the digits of the extremities(hands or feet) and more particularly to devices which are self-contained and which have more than one mode of use or application.

Traction systems and devices according to the invention may be applied to the digits of both hands and feet but for convenience the following discussion will be limited to the hand application.

Traction is indicated and potentially beneficial for a number of health conditions including arthritis and many devices are available. Application of a static tensile force to a digit requires, of course, a tension member which is fixed at both ends, one end connected to the digit and the other end anchored at a point fixed in relation to the point of attachment to the digit. Digital traction devices may be broadly classified into two groups according to the general location of the anchor or reaction point of the tension member. In the first group the anchor point is remote from the hand and its digits and may, with the help of an associated frame, be located on another part of the body such as the upper arm, or on the frame of a bed supporting the patient. In the second group, which may be classed broadly as self-contained, the anchor point is on the hand and/or wrist. These self-contained devices are potentially more compact and provide greater mobility for the patient.

The present invention is related to the self-contained group. Known devices in this class tend to be complex, requiring skilled application and custom fitting as well as being heavy and clumsy, offering serious hindrance to the patient's mobility and normal activities. Typically the ultimate anchoring point is the wrist or forearm so that the whole hand and the wrist itself is subject to whatever traction force is applied to the digit or digits, even though in some conditions whole hand traction is not indicated.

SUMMARY OF THE INVENTION

Accordingly, it is an object of the invention to provide a simple low-cost digital traction system capable of applying traction to all joints of a digit including the metacarpophalangeal joint and, optionally, to all digits of the hand or foot and lending itself to mounting, adjustment and management by the patient with a minimum of medical intervention.

It is also an object to provide a digital traction device which is light in weight and of low profile so as to offer minimum impedance to the mobility and activity of the patient. Preferably the device permits some use of the patient's hand in at least one mode of operation.

It is also an object to provide a digital traction system which is conveniently portable and which can be used satisfactorily for a wide range of hand sizes.

Another object of the invention is to provide a digital traction system which includes configurations offering at least two basic modes of operation. In both modes, the device is anchored near the base of the digit to be treated and both share at least some common components.

These objects may be realized in a digital traction system based on a common traction plate or frame which, in use, may normally lie generally parallel to the digits being treated, either on the back of the hand (dorsal position) or inside the hand (palmar position), and span the length of the fingers from near their root to a point adjacent to but preferably somewhat beyond the tips of the fingers. Traction may be applied individually to each digit by a separate elongated tension member having one end connected to the traction plate, and preferably passing over the outer end of the plate and returning, for attachment of the opposite end of the tension member to the digit to be treated. It is desirable that in operation the tension member be at a uniform tension over its entire length. Preferably, a low friction surface is provided at the outer end of the traction plate to facilitate this. A transversely extending roller may be used.

Clearly the arrangement just described results in the traction plate being biased toward the base or root of the digits and palm of the hand. And the inner end of the plate must of course be anchored. In one embodiment and mode of application a traction plate is disposed on the palm side or below the hand and is anchored by providing means for temporary adhesion of its inner end to the hand, closely adjacent the base of the fingers. In a preferred embodiment the temporary adhesion or releasable anchoring may be provided by using a fingerless glove and providing self connecting surfaces, such as hook and loop fabrics (of the type, for example, sold under the trademark "VELCRO"), on the registering and connecting portions of the traction plate and the glove.

In a second embodiment and mode of application a traction plate may be disposed on the back of the hand (dorsally) and anchoring of the inner end of the traction plate may be achieved by lugs extending from the plate and passing between the fingers and engaging a crotch between a pair of fingers, thus providing a stop or anchor so that the traction plate becomes a relatively fixed base for applying traction to the digits.

The preferred embodiments may include the use of a common traction plate and tension members and also a particular adaptation of the well-known Chinese finger trap as the input members for applying traction to the digit. The sleeve of the finger trap may be of braided strand construction, each strand consisting of a plurality of filaments of a pliable material such as polypropylene, bundled relatively loosely for improved comfort and efficiency of the finger trap. In this adaptation, the outer or distal end of the finger trap is open so that, if desired, the fingertip may protrude through and the tension member may be attached to the body of the finger trap at a point somewhat inset from its outer end. This arrangement helps to minimize the length of the traction plate and potentially contributes to the overall compactness and lightness of devices according to the invention.

Other features and advantages of a multi-mode digital traction system according to the invention will become apparent from the description which follows.

Figure 1:
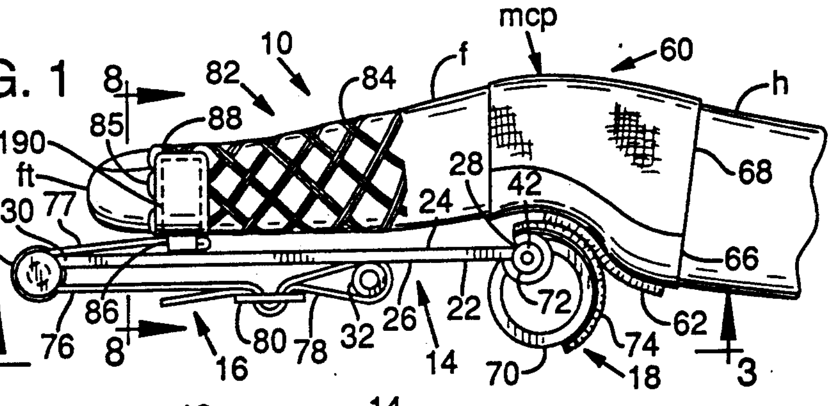
FIG. 1 is a side view of a digital traction system applied to a right hand with the traction producing elements mounted on the palm side of the hand. For clarity the thumb is omitted from the drawing.

This arrangement includes a separate subassembly for the thumb, seen in top view in the drawing.

Figure 3:
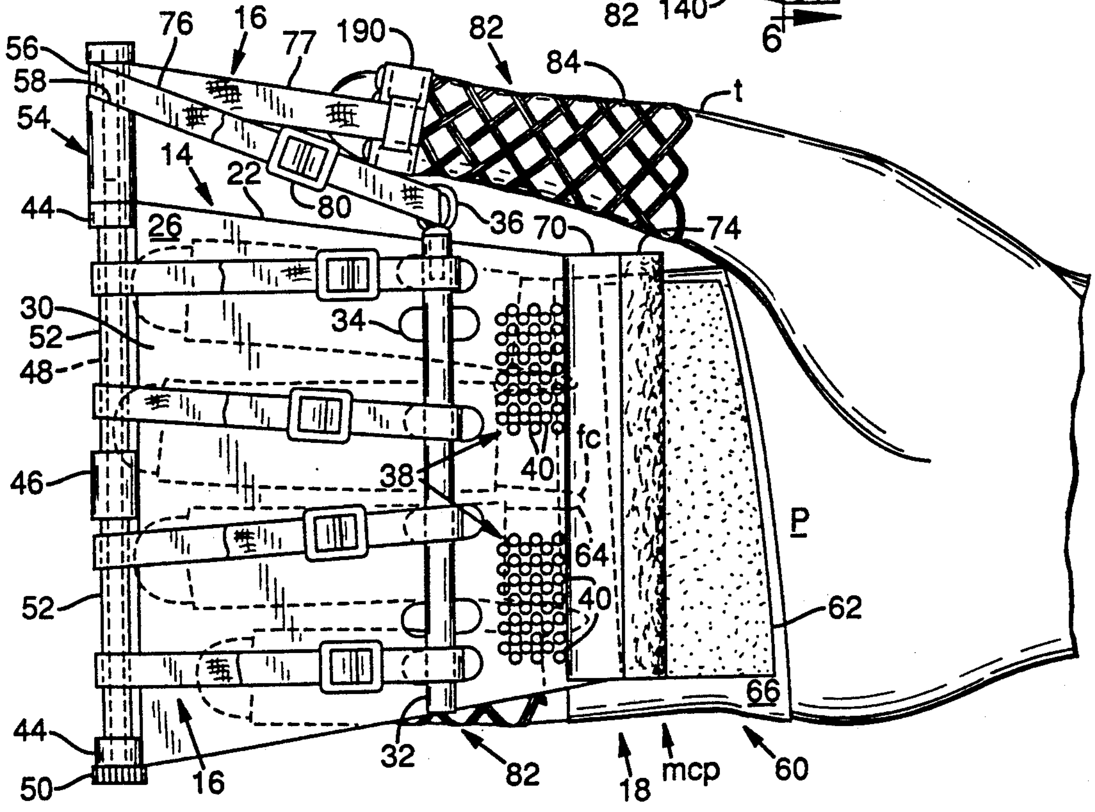

FIG. 3 is an inside or underneath view taken approximately on line 3—3 of FIG. 1, but including the thumb.

Figure 4:
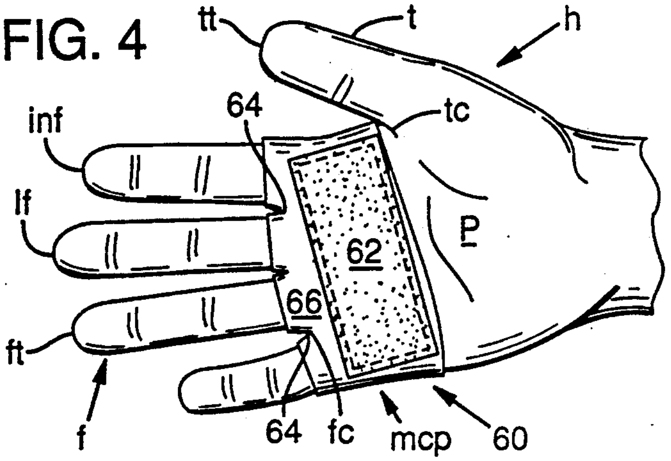

FIG. 4 is a view similar to FIG. 3 but to a reduced scale showing only the fingerless glove anchor member of the first embodiment.

Figure 2:
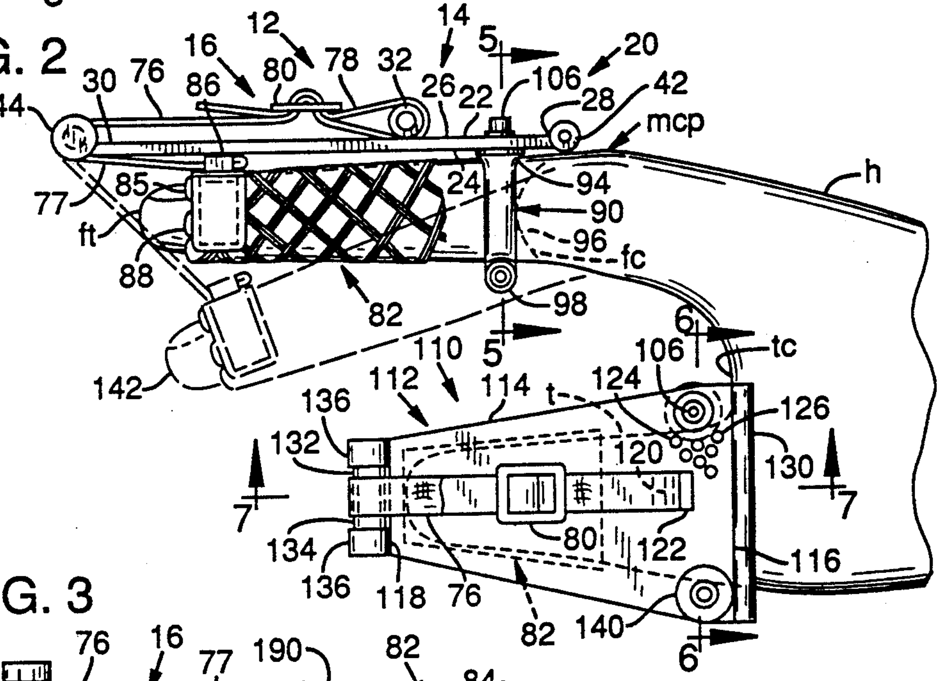
FIG. 2 is a view similar to FIG. 1 of a second embodiment of the invention but with the traction producing elements mounted dorsally on the outside of the hand.
Figure 5:
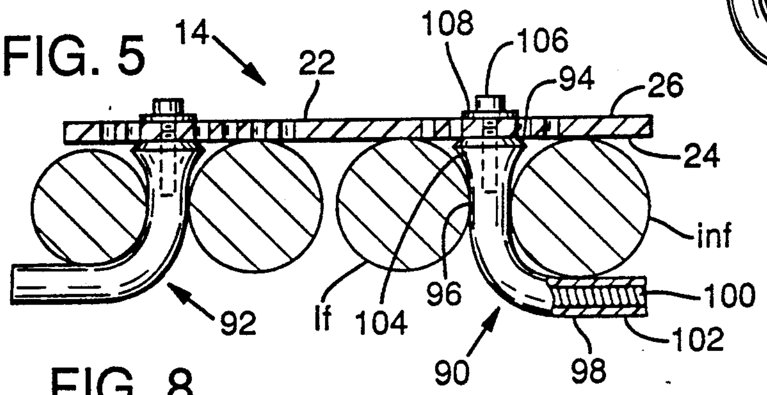

FIG. 5 is an enlarged cross-sectional view taken on line 5—5 of FIG. 2 showing in more detail the anchor elements of the second embodiment.

Figure 6:
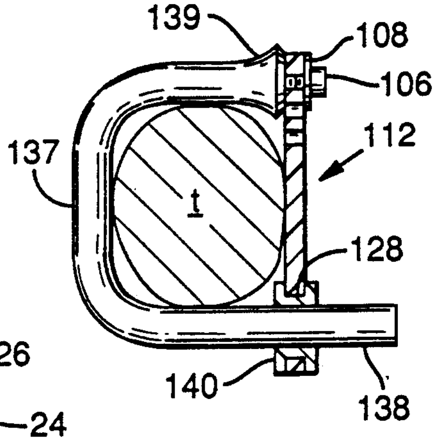

FIG. 6 is a cross-sectional view taken on line 6—6 of FIG. 2 showing in more detail, for the second embodiment, the anchoring and retaining arrangement for the thumb.

Figure 7:
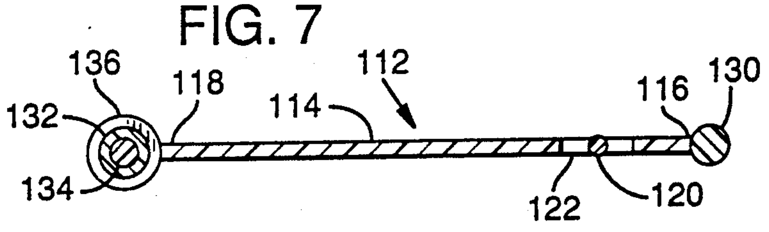

FIG. 7 is a center line cross-sectional view of the thumb traction subassembly of FIG. 2 taken on line 7—7 of FIG. 2.

Figure 8:
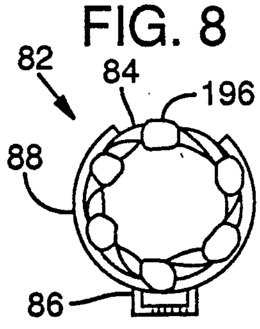

FIG. 8 is an end view of the connecting end of one of the finger traps of the system, taken on line 8—8 of FIG. 1.

Figure 9:
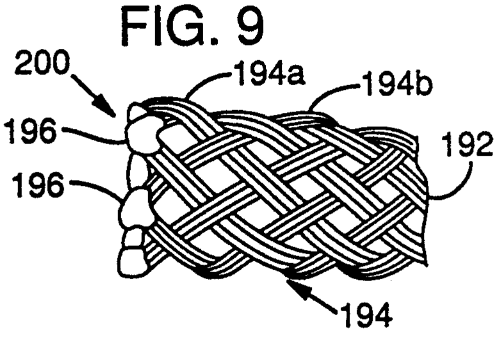

FIG. 9 is a somewhat enlarged partial view from FIG. 1 of the connecting end of one of the finger traps with the connecting patch removed to show more clearly the construction of the end of the finger trap.

Figure 10:
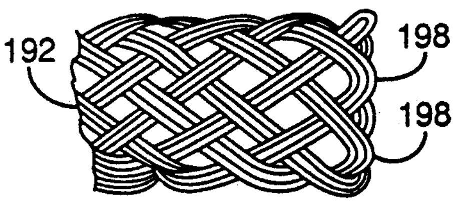

FIG. 10 is a partial view of the inner or proximal end of a finger trap showing an alternative end construction.

DESCRIPTION OF THE PREFERRED EMBODIMENT

The invention is embodied in the digital traction system 10 illustrated in a first embodiment and a first mode of application in FIGS. 1 and 3.

FIGS. 2, 5 and 6 illustrate a second embodiment 12 of the invention in a second mode of application.

The two embodiments 10, 12 use a common traction plate 14, and, optionally, one or more common traction transmission subassemblies 16. Both embodiments rely substantially on the crotch between the fingers (or between finger and thumb) for providing a stop or anchor to provide a traction force reaction. But in the first embodiment, the anchoring system 18, seen best in FIG. 1, loads the crotch fc of the fingers less directly than the anchoring arrangement 20 of the second embodiment, seen best in FIGS. 2 and 5.

Now, describing the digital traction system in more detail and, first, with particular reference to the first embodiment and FIGS. 1, 3 and 4—in the traction plate 14 a frame-like member, body 22, is preferably a relatively thin, relatively stiff, flat plate of a suitable material such as clear plastic. In this embodiment the generally laminar traction plate is mounted on the palm side of the hand. The body 22, trapezoidal in shape, has opposite surfaces, digit side 24 and tensor side 26. The parallel sides of the trapezoid comprise the shorter, inner anchor end 28 and the longer, outer tensor return end 30. As seen clearly in FIGS. 1 and 3, the traction plate body 22 is dimensioned so that the inner end 28 approximately matches the width of the palm p of the hand, the outer end 30 accommodates a comfortable spread of the fingers f of the hand, and the plate is of a length sufficient to extend somewhat beyond the fingertips ft.

A cleat bar 32, preferably of circular cross-section and with a smooth low friction surface, extends transversely on the tensor side 26 of the traction plate body 22. The cleat bar 32 overlays and approximately bisects a series of cleat slots 34 extending transversely across the body 22. In the present embodiment, one end of the cleat bar 32 carries a tensor holding loop or ring 36 (see FIG. 3). This holding element 36 may be threaded into the end of the cleat bar 32 so that it may be optionally mounted at either end. It may also be in the form of a hook or other suitable retaining shape and may be integral with the cleat bar 32 or mounted by any other suitable means at or adjacent the end of the cleat bar 32. A pair of spaced apart arrays 38 of mounting holes 40 perforate the traction plate body 22 close to its inner end 28. They are used in the second embodiment as described below.

Both the inner and outer ends of the traction plate body 22 are modified. The inner, anchor end 28 carries a bead 42 of diameter somewhat greater than the thickness of the traction plate body 22. The outer end 30 carries a series of three spaced apart coaxial bushings, end bushings 44 and an intermediate bushing 46. Both the anchor end bead 42 and the outer end bushings 44, 46 are preferably offset somewhat towards the tensor side 26 of the traction plate body 22 (FIG. 2).

A long bolt 48 with a flat knurled head 50 extends through the bushings 44, 46 and journals a pair of tubular rollers 52, captive between the bushings. A traction plate extender 54 is threaded onto the end of the bolt 48 and serves both to retain the bolt and to provide a positioning groove 56 for a tensor member (to be described below), the groove being defined in part by an inclined inner shoulder 58.

In the anchoring arrangement 18 of the first embodiment (FIGS. 1 and 3) the base member is a fingerless glove 60. As seen clearly in FIG. 4 the glove 60 may embrace only the four fingers of the hand and be only long enough to accommodate a rectangular patch 62 of hook and loop fabric such as that sold under the trademark VELCRO and include crotch elements 64 for engaging the crotches fc between the fingers. Preferably the glove 60 is stretchable to fit a range of hand sizes and may, for example, be of a construction used in many athletic gloves and including a palm member 66 of relatively thin leather and a back 68 of a stretch fabric.

Anchoring arrangement 18 is completed by a contoured anchor member adapter cylinder 70 which includes a longitudinal surface groove 72 which snugly slides on to the bead 42 at the inner end of the traction plate body 22 thus interlocking the traction plate 14 and the auxiliary anchor member, cylinder 70, and holding them in fixed relationship. A second patch 74 of hook and loop fabric is fixed on the cylinder 70 and covers about half its surface extending circumferentially from the groove 72. In assembly, and as seen best in FIG. 1, the hook and loop patches 62, 74 register and are adjustably engageable so as to fix substantially the position of the traction plate 14 relative to the hand. A convenient interlocking form of attachment for the adapter 70 (groove 72) has been shown but clearly other forms of attachment could be used.

Each traction transmission arrangement 16, includes a tension member, a thin narrow elastic band or tensor 76 formed in a loop 78 around the cleat bar 32 and adjustably secured by a buckle fastener 80. The elastic band/tensor 76 passes over one of the rollers 52 and returns (77) on the digit side 24 of the traction plate 22 for attachment to a finger f. (For thumb traction in this first embodiment the tensor 76 is trained over the groove 56 of the traction plate extender 54). In these exemplary embodiments traction is ultimately applied to the digit by a finger trap 82 which, for gripping the digit, uses the principle of the well-known so-called Chinese finger trap. The body or sleeve portion 84 of the finger trap is formed from braided strands forming a sleeve which, when relaxed, slides easily onto the digit. When the outer ends of the strands are grasped attempts to withdraw the finger are defeated by the sleeve 84 contracting and gripping the finger. In this exemplary embodiment, attachment of the elastic band/tensor member 76 to the finger trap 82 is made by securing the tensor 76 in a sleeve 86 fixed to a flexible connection plate or patch 88. Preferably, the connecting element or sleeve 86 is disposed so that, in assembly, it is inset from the end of the sleeve 84. Connection patch 88 at least partially wraps and is fixed to, by some suitable method such as stitching 190, the outer end of the finger trap sleeve 84.

Looking in more detail at the construction of the sleeve 84 of the finger trap 82 and referring particularly to FIGS. 8, 9 and 10—the basic element of the sleeve is a pliable filament 192, a plurality of which are bundled loosely in each strand 194. Polypropylene is a preferred material for the filaments 192. Preferably, in each strand, the filaments 192 lie loosely together substantially linearly as indicated in FIG. 9 (they are not twisted, in rope fashion). The strands 194 are conventionally braided together to produce an open center sleeve or tube 84 which, when extended axially, contracts in diameter (similar to a Chinese-finger trap). The braiding defines right-hand and left-hand spiral strands 194*a*, 194*b* respectively. The ends of the sleeve 84 are formed or terminated by bonding or cementing together at joints or nodes 196, pairs of strands consisting of one right-hand and one left-hand strand 194*a*, 194*b* at their crossover points. Preferably all the filaments of each strand are captured at each bonded joint 196. It is noted that this form of sleeve 84 is similar to that which would be obtained from a suitable "off the shelf" hollow braided rope, cut to length at suitable points related to the braid pattern, and with the strand ends secured as described above. In another form (FIG. 10) the braid may be formed with the "connecting" left and right-hand strands being continuous so that at one end of the sleeve the terminations are in loops 198.

Connecting patch 88 may, in the flat, be rectangular and made of a suitable, thin, flexible material such as nylon sheet. The stitching 190 of the connecting patch 88 to the strands 194 of the sleeve may also be of nylon. The stitching 190 should embrace a substantial number of the filaments 192 of the strands 194 which it wraps so as to be firmly anchored to the strands and positively transmit an applied traction force into the sleeve as a whole. A connecting patch 88 which wraps the end of the sleeve 84 by at least more than half its circumference is preferred. In part, this arrangement distributes the traction force sufficiently uniformly into the strands 194 of the sleeve 84. At the same time, this incomplete encirclement allows the connecting end 200 of the sleeve to adjust in diameter as required along with the sleeve as a whole to accommodate a particular finger size.

Turning now to the second embodiment and referring particularly to FIGS. 2 and 5—the traction plate 14 and traction transmission arrangement 16 are the same as those used in the first embodiment. But a different anchoring arrangement 20 is used to anchor the traction system on the hand. In this case, traction lugs 90, 92 are mounted on the traction plate 14, each lug making use of one of the mounting holes 40 in the hole arrays 38. The larger lug 90 is preferably used between the index finger inf and long finger lf as shown in FIG. 5. The lugs or stop members 90, 92 are similar in construction and only one need be described. Functional requirements of the lug or stop member 90 are to provide a "stop" preventing retraction of the traction plate 14 due to the pull of tension member portion 77 and fitting comfortably against a finger crotch fc, mounted upright on or generally perpendicular to the traction plate body 22 and bent over so as to engage the digit and hold the traction plate 22 reasonably snugly against the base of the digit. Preferably the lug 90 has a belled or conical root 94 for stability of mounting and more comfort, a straight crotch portion 96 and a bent over tail or retainer portion 98. Preferably the lug 90 is flexible for easier mounting and comfort. A suitable construction may consist of a closely wound spring core 100 covered by a latex rubber tube 102 and a plastic bell member 104 at the inner end. Mounting of the lug 90 to the traction plate 22 may be made by any suitable method such as threading a socket head screw 106 into the inner end of the spring core 100, either directly as suggested by the drawings or into a threaded insert (not shown). When a threaded mounting arrangement is used for the lug 90 and a load spreading washer 108 is used the screw 106 may be left slightly loose so that the lug 90 may swivel relative to the plate 22, further facilitating mounting and dismounting of the device.

Although, in the second embodiment, thumb traction may be provided by making use of the traction plate extender 54 as in the first embodiment (See FIG. 3), it is preferred to use a separate thumb traction arrangement 110 as illustrated in FIGS. 2, 6 and 7. The general construction and anchoring arrangement are similar to that used for the fingers. A tapered traction plate 112 includes a body 114 having an inner, anchor end 116 and an outer end 118. A short cleat bar 120 of circular cross section is fixed transversely in an oval slot 122. There is a single array 124 of mounting holes 126 towards a corner of the plate adjacent the inner end 116. In the opposite inner corner there is a through hole 128. The inner end 116 of the plate carries a bead 130 similar to the bead 42 of traction plate 14. At the outer end 118 a roller 132 is freely rotatable on a pin 134 and captive between a pair of bushings 136. For retaining the traction plate 112 against the thumb and stopping it against the thumb crotch tc, a holding band 137 is used. It may be similar in form, function and construction to the lug 90 described above except that it has a tail 138 for passing through the hole 128 and so as to completely wrap the thumb t. The tail 138 is pulled through the hole 128 for a comfortable fit on the thumb t. Preferably friction between the tail 138 and the hole 128 secures the holding band 137 in adjustment. In the exemplary construction shown a rubber grommet 140 is used as a friction device. Note that in the separate auxiliary thumb traction plate 112 the inner end bead 130 and the bushings 136 at the outer end are carried symmetrically with regard to the thickness of the body 114.

Turning now to the assembly and mounting and to the features and advantages of the invention, first with particular reference to the first embodiment and first mode of application as illustrated in FIGS. 1, 3 and 4—assembly may begin by pulling the fingerless glove 60 onto the hand h (right-hand is assumed) so that the crotch members 64 of the glove are snugly against the finger crotches fc. This places the hook and loop pad 62 in the palm of the hand and close to the base of the digits and hence to the metacarpophalangeal joints mcp to be treated, in this case those of the fingers f. A glove embracing only the four fingers, as in the illustrated glove 60, is adequate for its purpose. Absence of the thumb makes the glove easier to mount and suitable for both left and right hand use. However, a longer glove with a thumb member may be used if desired.

Next the traction plate 14, complete with adapter cylinder 70, and the traction transmission members 16 may be assembled together in the configuration shown in FIGS. 1 and 3 with the buckle fasteners 80 of the tensor bands 76 used to set the unstretched length of the tensors in anticipation of the degree of traction to be applied. Then the finger traps 82 may be slid onto each digit. The positioning of each trap longitudinally along its digit is guided by comfort and/or the intended point of application of the traction. Only one reference numeral 82 has been applied to the finger traps, but in fact they may be of varying sizes to suit the typical range of finger sizes found in the human hand.

The open-ended finger trap, as well as contributing to the compactness of the system, may aid in patient comfort and satisfaction by leaving the fingertip exposed for some tactile activity and limited use of the hand in grasping, at least in the embodiment of FIG. 2. This is suggested by the removed position 142 of one of the fingers f in FIG. 2. Although not shown in the drawings, all of the fingers may be flexed at the same time (from the metacarpophalangeal joint), in which case the traction board 14 would remain close to the dorsal side of the fingers.

The particular sleeve (84) construction and choice of materials also contribute to superior finger trap performance and comfort. The sleeve 84 retains its resilience and a high coefficient of restitution to its original relaxed form even after many uses so that it can continue to grip the digit readily and consistently. A relatively loose arrangement of the filaments 192 in the strands 194 allows the strands to spread on contact with the digit, conforming to its surface, bringing many filaments 192 into contact with the digit and so spreading the load for a comfortable but reliable grip.

An object of the present invention is to provide a particularly light and compact traction device. In keeping with this object, a finger trap 82 having a sleeve member 84 open at the tip end 85 and providing a connection point (sleeve 86 on connecting patch 88) inset from the end of the sleeve 84 permits making the connection of the tensor 76, relative to the finger, at a point substantially inset from the finger tip ft. Thus, the traction plate 14 need not extend substantially beyond the finger tip, if at all, but still provide sufficient longitudinal space for a functionally adequate length 77 of tensor on the digit side 24 of the traction plate. Thus compactness in terms of traction plate length is achieved. Clearly, provision of a "return configuration" (rollers 52) for the tensors 76 also contributes to compactness. The same length of tensor 76 stretched on only one side of the traction plate (14) would require a much longer traction plate. However, although less compact, such a traction plate and tensor configuration could be used satisfactorily with the anchoring arrangements (18, 20) and finger attachment (82 or other) of the invention.

With the digits engaged within the finger traps 82 and the tensors 76 trained around the rollers 52, the traction plate 14 may be brought into position alongside the palmar side of the fingers. The hook and loop pad 74 on the adapter cylinder 70 can then be brought into engagement with the mating pad 62 on the glove 60 in a position comfortable for the patient and anchoring the traction device close to the base of the digits or metacarpophalangeal joints mcp to be treated. Typically this mounting sequence will have placed an initial tension in the tensors 76. Final tension may be set as required using the buckle fasteners 80 for adjustment. The separable nature of the two components (adapter cylinder 70, glove 60) of the anchoring arrangement 18 provides some basic adjustment of the fit or relative longitudinal position of traction plate 14. The overlapping extent of the hook and loop fastener or pads 62, 74 provides this latitude.

In an alternative method, the traction plate 14 may be mounted to the hand first. Then each finger trap 82 may be mounted on its finger after training the tensors 76 around the rollers 52.

The mode of application shown in FIG. 1 and whose method of mounting has just been described, is an inside or palmar application of the device with respect to the positioning of the traction plate 14. In this mode the digits are substantially immobilized, although some limited flexing of the phalangeal joints in the direction of closing the hand is feasible and, of course, the metacarpophalangeal joints mcp are unencumbered and free to articulate. In this mode however, the thumb is relatively free as the use of the traction plate extender 54 does not require that the traction plate underly the thumb as it does the fingers.

Essentials of the tension members tensors 76 is that they be elastic, suitably flexible, that they have a "spring rate" suitable to the application and, preferably, that that spring rate is maintained in prolonged and repeated use of the device. Clearly for consistent application of the desired traction to the digit, the outer end 30 of the traction plate body 22 must provide a tension member return surface little frictional resistance to relative movement of the tensor 76 offering where it reverses direction or returns to connect with the finger trap 82. The exemplary preferred embodiment uses freely rotating rollers 52 but other arrangements are possible given suitable material selection, both for the traction plate body 22 and the tensor 76, such as a smooth rounded edge or bead at the outer end 30, integral with the traction plate body 22. Provision of the inclined shoulder face 58 on the traction plate extender 54 helps to minimize friction in the thumb tensor if the application configuration results in a side load at this contact point. If thumb traction is not indicated, the traction plate extender 54 may be replaced by a simple nut (not shown in the drawings). Elastic cords are shown as an exemplary embodiment of tensor 76. The tensor or tension member could, of course, take other forms such as a combination of extension spring and inelastic cord.

A given basic size of traction plate 14 may be fitted to a range of hand sizes, in part due to the provision of extra slots 34 offering a choice of lateral spacing for anchoring the tensors 76. The trapezoidal shape of the traction plate provides a wider outer end 30 so that the tensors 76 may be splayed or fanned out as required to match the particular digit spread of an application.

The traction plate 14 is basically symmetrical about a longitudinal center line so that it may be used equally on the left or right-hand. In the first mode (FIGS. 1, 3) the digit side 24 of the plate is upwards (towards the palm), on both hands. In the second mode (FIG. 2) the digit side 24 is down (towards the dorsal side of the hand), on both hands. If they are detachable, the traction plate extender 54 and the cleat bar loop 36 (both for the thumb), may both be relocated at the opposite side of the traction plate as required. Or, as suggested above, a permanent anchor point for the thumb tensor may be provided a both sides of the traction plate in place of the removable ring 36. A traction plate extender similar to extender 54 of the present embodiment may also be provided on both sides of the traction plate, possibly permitting some simplification of manufacture, but the projection of the unused extender may make this arrangement less desirable. A "solid" traction plate body 22 has been disclosed but clearly, while retaining its generally planar nature, it could take another form, such as an open frame.

Turning now to the assembly and mounting and to the features and advantages of the second embodiment and second mode of application of the invention as illustrated in FIGS. 2 and 5 and, by optional extension, FIGS. 6 and 7—assembly may begin by positioning the crotch lugs 90, 92 to suit the hand by mounting them in suitable holes 40 in the hole arrays 38 and securing them with screws 106 and washers 108, either fixed or free to swivel as described above. With the traction transmission assemblies 16 preassembled and connected to cleat bar 32 in the configuration shown in FIG. 2, the traction plate 14 may now be positioned on the back or dorsal side of the digits with the crotch lugs 90, 92 snugly positioned in the crotches fc of the fingers. Each finger trap 82 may then be slid onto its respective digit, carefully training the tensor bands 76 around the rollers 52, with final adjustment of tension as required. In this mode of application, with the traction plate mounted dorsally, considerable mobility of the individual digits is retained, especially in the metacarpophalangeal joint, mcp as suggested by the removed position 142 of one of the digits indicated in FIG. 2. In this second embodiment the symmetry of the traction plate again makes it suitable for both left and right-hand use.

Thumb traction in the second embodiment may be provided for by use of the traction plate extender 54 in the same way as in the first embodiment (such an arrangement is not shown in the drawings). However such use may not provide the desired alignment of the tensor 76 with the thumb and may also impair mobility of the thumb. It is preferred to use the optional independent thumb traction arrangement 110 illustrated in FIGS. 2, 6 and 7 and described in detail above. Its features and mode of application have much in common with the second embodiment as applied to the fingers. However, in this case the plane of symmetry making the thumb traction plate 112 usable (by inversion) for both left and right thumbs is a central plane bisecting the thickness of the traction plate body 114. This permits, in both left and right-hand applications that, for comfort and proper support, the enlarged bell shaped portion 139 of the holding band 137 may be positioned in the thumb crotch tc while maintaining the same wrapping configuration of the tensor band 76 with respect to the traction plate 112 and the finger trap 82. The conversion or assembly to make the independent thumb traction assembly 110 either left-hand or right-hand is made by assembling the holding band 137 on the appropriate side of the traction plate 112.

It will be understood that the embodiment of FIG. 2 could also be applied inverted, with the traction plate 14 mounted inside on the palmar side of the hand, but this is not shown in the drawings.

A multiple mode, digital traction system according to the invention is simple, light and compact and potentially low in manufacturing cost and provides a high degree of commonality or interchangeability of components both between first and second modes of application and between left- and right-hand usage. Components of a single size may accommodate a wide range of hand sizes. Assembly or reassembly to establish desired mode of operation (palmar or dorsal for example) or to prepare for left or right-handed use may easily be done by the patient or others without special tools or equipment. Independent adjustment of degree of traction for each digit is also simply made and may be controlled by the patient if desired.

An advantage of systems according to the invention is that, as is clear from the drawings and above description, a traction plate or frame is anchored to the extremity solely by attachment or anchoring adjacent the metacarpophalangeal joints (in the hand application). But the traction plate remains substantially free of the digits and all of the phalangeal joints are substantially unencumbered by the anchoring means and free to articulate while under traction, at least partially, in both embodiments.

The invention is enhanced by a particular construction and configuration of finger trap which contributes to the compactness and efficiency of the system and also to patient comfort. Those of ordinary skill in the art will recognize useful variation of the embodiments and modes of application described above falling within the scope of the invention and intended to be embraced by the claims which follow.

I claim:

1. A traction system for the digits of a human extremity, each digit having a base and a palmar side and the extremity having a plurality of crotches between the digits comprising:

a longitudinally extending traction plate for laying longitudinally alongside the palmar side of at least one of the digits, the plate having a free end and, longitudinally spaced from the free end, an anchor end;

means for anchoring the plate anchor end to the extremity including a glove carried by the extremity and a contoured anchor member carried by the plate anchor end said member having a curved portion for engaging the glove and remaining in fixed relation with the extremity, said anchoring being effected solely by direct engagement of the anchoring means with the extremity adjacent the base of the at least one of the digits, the plate, in use, being substantially free of the at least one of the digits and said anchoring leaving all of the digits substantially unencumbered; and at least one elongated tension member extending generally longitudinally and having an end attached to the traction plate and an opposite end, the opposite end including means for attachment to a digit so as to apply a traction force to that digit.

2. The system of claim 1 wherein the contoured anchor member is detachable from the traction plate.

3. The system of claim 1 wherein the contoured anchor member is generally cylindrical and, in use, extends generally transversely of the extremity.

4. The system of claim 1 and including means for providing a releasable connection between the contoured anchor member and the extremity.

5. The system of claim 4 wherein the means for providing the releasable connection includes mating hook and loop type fabric surfaces, one surface on the glove and one on the contoured anchor member.

6. The system of claim 1 wherein the glove includes a digit covering portion and said portion is abbreviated so that the digits are substantially unencumbered by the glove.

7. The system of claim 1 wherein the means for attachment of the tension member to the digit includes a sleeve for fitting over the digit the sleeve, upon the application of a tensile force, contracting in diameter so as to grip the digit.

8. The system of claim 1 wherein the free end of the traction plate includes a tension member return surface over which the at least one tension member is trained.

9. The system of claim 1 wherein the traction plate includes a transversely extending tension member attachment portion for receiving the attachment of the at least one tension member.

10. The system of claim 1 wherein the traction plate and the means for anchoring comprise an independent unit for application to a single digit of the at least one of the digits.

11. A finger trap for use in applying traction to a digit of a human extremity, of the type which contracts to grip the digit upon the application of a traction force to the distal end of the trap comprising:

an elongated braided sleeve having opposite ends and being open at both ends, the sleeve including a plurality of strands the strands being formed into respective left- and right-hand spirals, each strand being an element of the braid and comprising a bundle of individual filaments; and a flexible connection patch for connecting to a tension member for applying the traction force, the patch being carried by the sleeve adjacent one of its opposite ends and making force transmitting contact with a plurality of the strands.

12. The finger trap of claim 11 wherein the connection patch is stitched to the sleeve.

13. The finger trap of claim 11 wherein the connection patch partially wraps the end of the sleeve.

14. The finger trap of claim 11 wherein the connection patch includes a connecting element for receiving the tension member and said connecting element is inset from the end of the sleeve.

15. The finger trap of claim 11 wherein, in each strand, the filaments lie loosely together in substantially linear alignment.

16. A traction system for applying traction to at least one of the metacarpophalangeal joints of a hand, the hand having a plurality of digits and crotches between the digits, the system including a traction frame for anchoring to the hand and means connectable between at least one digit and the frame for applying a traction force through the digit to the corresponding metacarpophalangeal joint characterized in that the system includes a glove conforming to and covering at least part of the hand and, in use, the traction frame is anchorable to the hand solely by engagement of the traction frame with the glove at the palm of the hand adjacent the metacarpophalangeal joints so that the corresponding metacarpophalangeal joint is under traction.

17. The traction system of claim 16 wherein the traction frame extends generally longitudinally of the hand and includes a free end disposed, in use, adjacent the tips of the digits and an anchor end disposed and anchored adjacent the metacarpophalangeal joints.

18. The traction system of claim 16 wherein the traction frame has a lateral extent spanning at least two digits.

19. The traction system of claim 16 wherein the glove includes means for engaging the crotches between the digits so that, in use, retraction of the traction frame is resisted substantially by the crotches.

20. The traction system of claim 19 wherein, in use, the traction frame releasably engages the glove adjacent the metacarpophalangeal joints.

21. A traction system for applying traction to at least one of the metacarpophalangeal joints of a hand, the hand having a plurality of digits and crotches between the digits, the system including a traction frame for anchoring to the hand and means connectable between at least one digit and the frame for applying a traction force through the digit to the corresponding metacarpophalangeal joint characterized in that the system includes a glove configured to be pulled onto the hand so as to engage at least one of the crotches between the digits and in that the traction frame is anchored to the hand by means of the glove and so that, in use, retraction of the traction frame under the action of the traction force applying means is resisted substantially by engagement of the glove with the at least one of the crotches between the digits.

22. The traction system of claim 21 wherein the glove is configured to expose a substantial portion of the at least one of the digits for facilitating connection of the traction force applying means.

23. The traction system of claim 21 wherein the traction frame extends generally longitudinally and includes longitudinally opposite free and anchor ends and the glove includes a palmar side covering at least part of the palm of the hand and, in use, the anchor end is attached to the palmar side of the glove adjacent the metacapophalangeal joints.

24. The traction system of claim 23 wherein the anchor end of the traction frame is releasably attached to the palmar side of the glove at a selectively variable point of attachment.

25. The traction system of claim 21 wherein the traction frame has a lateral extent spanning at least two digits.

26. The finger trap of claim 11 wherein the filaments are made from polypropylene.

* * * * *